United States Patent [19]

Ovil et al.

[11] Patent Number: 4,898,155
[45] Date of Patent: Feb. 6, 1990

[54] SUTURING IMPLEMENT PARTICULARLY USEFUL IN SURGICAL OPERATIONS FOR THE ATTACHMENT OF A PROSTHETIC VALVE

[75] Inventors: Yoel Ovil, Ramat Hasharon; Morris Levy, Tel-Aviv, both of Israel

[73] Assignee: Galil (Naharia) Advanced Technologies Ltd., Ramat-Gan, Israel

[21] Appl. No.: 779,980

[22] Filed: Sep. 25, 1985

[30] Foreign Application Priority Data

Sep. 26, 1984 [IL] Israel ............................................. 73081

[51] Int. Cl.⁴ .......................... A61B 17/04; A61B 17/06
[52] U.S. Cl. ................................................. 606/144; 606/146
[58] Field of Search ............... 128/335, 334 R, 303 R, 128/340; 227/19

[56] References Cited

U.S. PATENT DOCUMENTS 3,409,013  11/1968  Berry ............................... 128/303 R
4,185,636  1/1980  Gabbay et al. ................. 128/334 R

FOREIGN PATENT DOCUMENTS 0850051  7/1981  U.S.S.R. ......................... 128/334 R

Primary Examiner—Edward M. Coven
Assistant Examiner—Gary Jackson
Attorney, Agent, or Firm—Benjamin J. Barish

[57] ABSTRACT

A suturing implement particularly useful in surgical operations for suturing a member, such as a prosthetic valve, to tissue at the suture site by a plurality of sutures each including a needle attached to at least one end. The implement comprises a manually grippable handle; pledget gripping members carried by the handle for gripping a plurality of pledgets each in a position to be pierced by a suture needle; and a releasing device carried by the handle for actuating the pledget gripping means to release the pledgets and the sutures applied thereto from the handle.

19 Claims, 3 Drawing Sheets

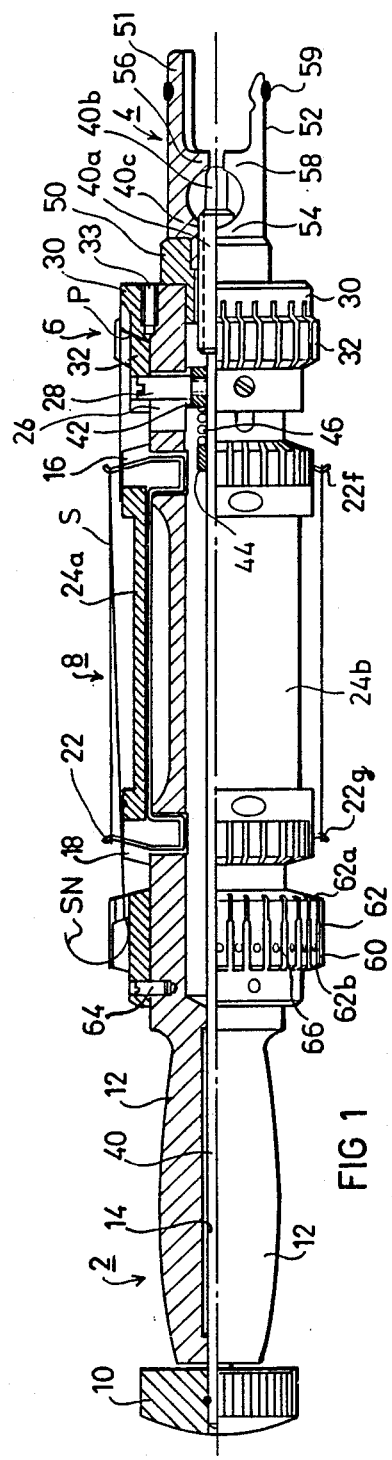
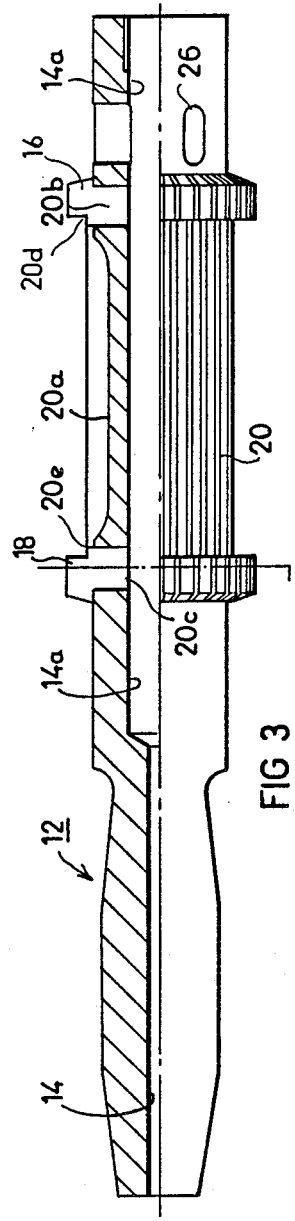
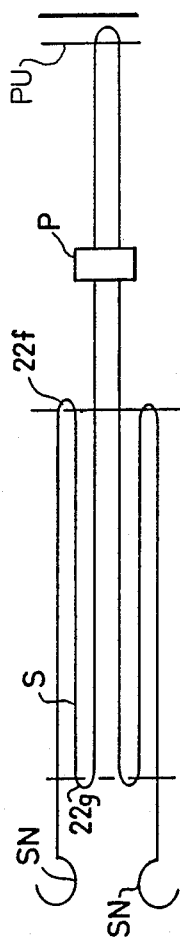
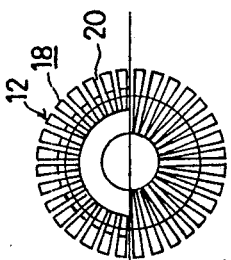

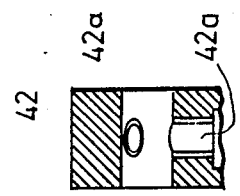
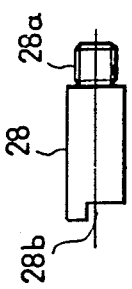
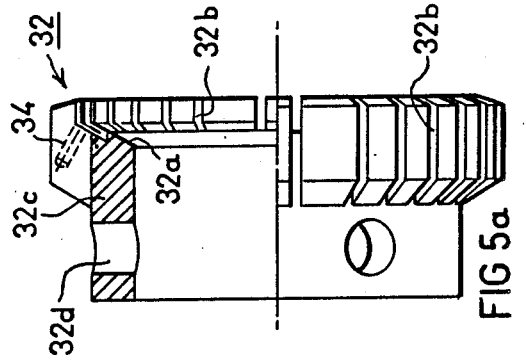
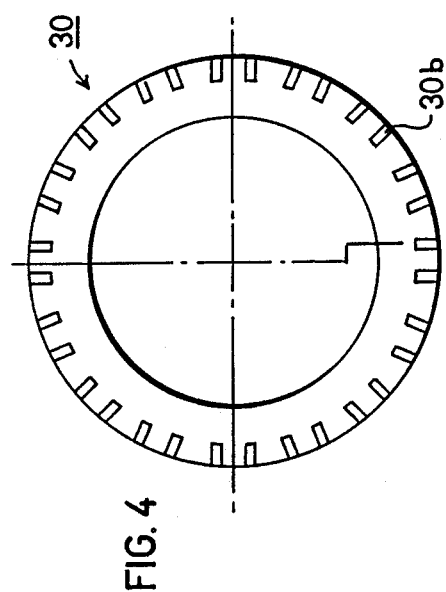
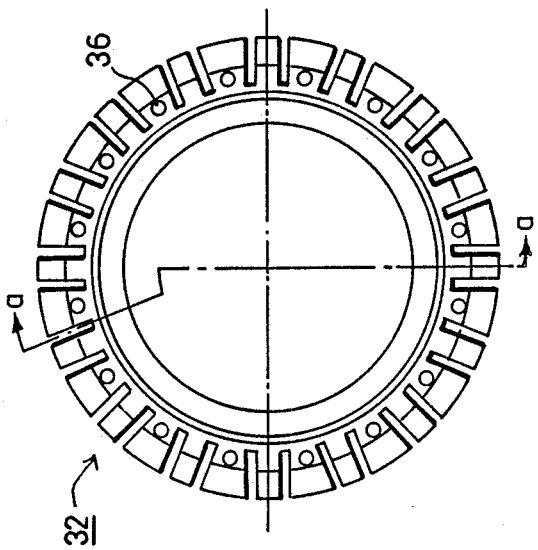
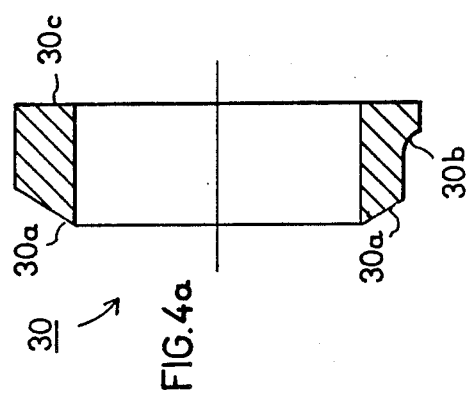

FIG.8a
FIG.8
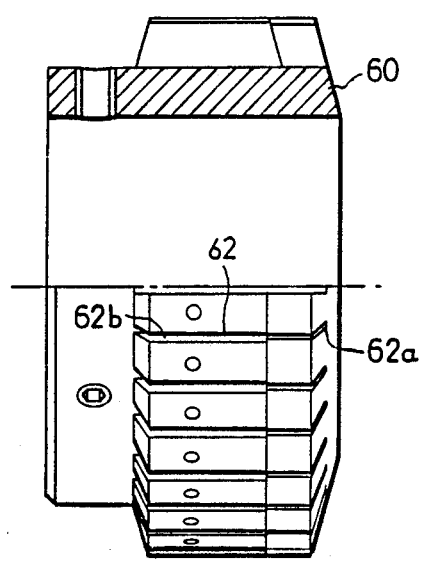
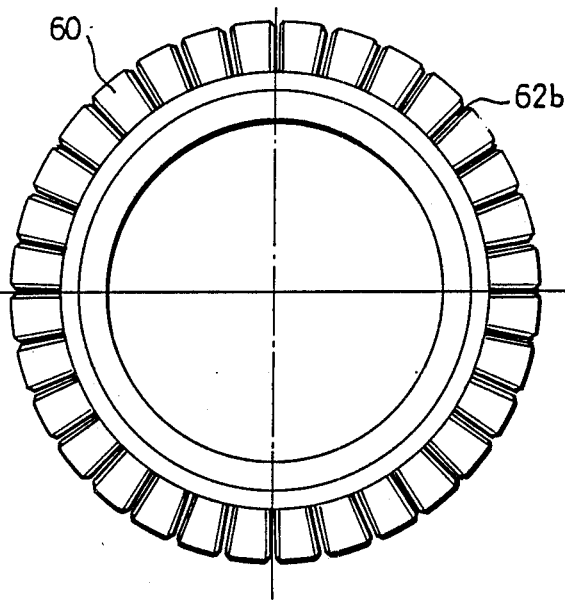
FIG 9
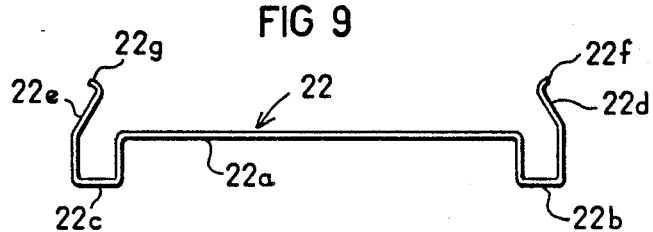
FIG 10
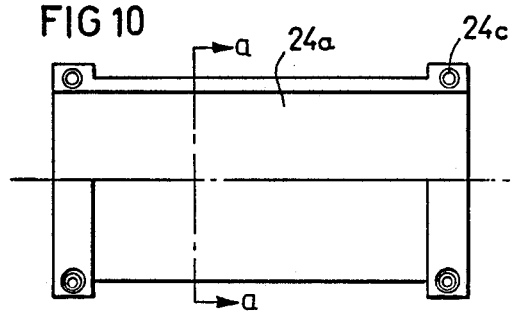
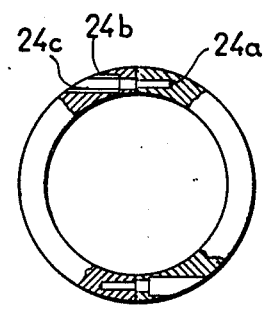
FIG.10a // SUTURING IMPLEMENT PARTICULARLY USEFUL IN SURGICAL OPERATIONS FOR THE ATTACHMENT OF A PROSTHETIC VALVE

BACKGROUND OF THE INVENTION

The present invention relates to suturing implements for use in applying sutures or threads. The invention is particularly useful in surgical operations for suturing a member, especially a prosthetic valve, to tissue at the suture site, and the invention is therefore described below with respect to this application.

The surgical replacement of defective heart valves, both the aortic valve and the mitral valve, has become a widely-practiced technique. In such a surgical operation, the defective natural valve is surgically removed, and a prosthetic valve is applied by a number of sutures, varying from 12-20 depending upon the size of the annulus remaining after removing the defective natural valve. In this surgical operation, the prosthetic valve to replace the natural one is usually held in a holder while each of the sutures is individually applied, first to the annulus and then to the valve on the holder; and after all the sutures have been applied to both, the valve is moved into the annulus and is fixed in place by knotting the sutures and trimming their ends. The existing procedures using valve holders and other implements presently available take a considerable length of time because of the large number of sutures which must be applied first to the annulus, and then to the valve, before the valve is moved into position within the annulus. Moreover, such a procedure requires a large number of attendants, particularly because of the many different tissues and different tissue points which must be maintained retracted during the surgical operation. Another very serious difficulty involved in the existing procedure is the danger of entanglement of the sutures because of their large number, and also because of their substantial length which is needed to enable the sutures to be applied to the body annulus and to the valve while the valve is held externally of the body, before the valve can be moved into the body annulus. All these drawbacks in the existing procedures using the presently available implements increase the time required for the surgical operation, the danger to the patient, the fatigue of the surgeon, and the number of attendants required for assistance.

Two surgical techniques are mainly used at the present time in the attachment of a prosthetic valve. One technique uses an "over-and-over" stitch when attaching the valve to the body annulus. A suturing implment particularly useful for this technique is described in our co-pending U.S. patent specification No. 69,635 filed Sept. 2, 1983.

Another popular technique uses a "mattress" stitch including a plurality of pledgets, namely small plastic pressure pads such as of "Teflon" (Reg. T.M.), which distribute over a larger surface the pressure applied by each suture to the body annulus. In this technique, each suture carries a needle at both ends, and each pledget is pierced by both needles of its respective suture. The pledget is applied to the outer side of the body annulus, and the suture is knotted at the inner side of the body annulus.

This "mattress" stitch technique, as presently practiced, is subject to all the above-described drawbacks applicable to the "over-and-over" stitch technique, with the additional drawback that the need to pierce the pledgets by the suture needles further increases the time required for the surgical operation, the danger to the patient, the fatigue of the surgeon, and the number of attendants required for assistance. A still further drawback in this technique, is that by knotting the sutures on the artificial valve itself, there is a possibility that the knot may interfere with the prosthetic valve such as to cause it to mal-function, thereby increasing the danger to the patient.

SUMMARY OF THE INVENTION

An object of the present invention is to provide an implement particularly useful for applying sutures or stitches which include the above-mentioned pledgets. A particular object of the invention is to provide a suturing implement particularly useful in surgical operations for attachment of a prosthetic valve.

According to a broad aspect of the present invention, there is provided a suturing implement particularly useful in surgical operations for suturing a member, such as a prosthetic valve, to tissue at the suture site by a plurality of sutures each including a needle attached to at least one end thereof, comprising: a manually grippable handle; pledget gripping means carried by said handle for gripping a plurality of pledgets each in a position to be pierced by a suture needle; and releasing means carried by the handle for actuating the pledget gripping means to release the pledgets and the sutures applied thereto from the handle.

In the preferred embodiment of the invention described below, the pledget gripping means grips the plurality of pledgets while in the form of an annular array around the handle. Such gripping means comprises a pair of annular members adapted to receive between them the annular array of pledgets, one of the annular members being movable by the releasing means toward and away from the other annular member to grip and release the plurality of pledgets.

According to a further feature in the described preferred embodiment, the pair of annular members are formed with axially-extending grooves for guiding the suture needle when applied to pierce the pledgets.

According to a further feature in the described preferred embodiment, the implement also includes suture retaining means for releasably retaining a plurality of sutures in folded condition on the handle. The latter retaining means retains the sutures in the form of an annular array on the handle with the sutures spaced circumferentially from each other and folded axially with respect to the handle.

According to still further feature in the described preferred embodiment, the implement also includes a holder at one end of the handle for releasably holding the member, such as a prosthetic valve, to be sutured.

Such a suturing implement is particularly useful in surgical operations for the attachment of prosthetic valves by the use of the above-described pledgets; and when the implement is so used, it enables a number of important advantages to be obtained over existing techniques, as will be described more particularly below.

BRIEF DESCRIPTION OF THE DRAWINGS

The invention is herein described, by way of example only, with reference to the accompanying drawings, wherein:

FIG. 1 is a view, partly in section, illustrating one form of suturing instrument constructed in accordance with the present invention;

FIG. 2 is a diagram illustrating the folded condition of each of the sutures when loaded in the implement of FIG. 1;

FIG. 3 is a side elevational view, partly in section, illustrating the main body member in the suturing implement of FIG. 1, FIG. 3A being an end elevational view of FIG. 3;

FIGS. 4 and 5 are end elevational views illustrating the two annular members included in the pledget gripping means of the implement of FIG. 1, FIGS. 4A and 5A being sectional views along lines a—a of FIGS. 4 and 5, respectively;

FIG. 6 illustrates one of the pins included in the pledget gripping means in the implement of FIG. 1;

FIG. 7 illustrates a locking ring in the implement of FIG. 1 for locking and releasing the pledget gripping means;

FIG. 8 is an end view of an annular member included in the implement of FIG. 1 for releasably retaining the sutures in folded conditions thereon, FIG. 8A being a sectional view along lines a—a of FIG. 8;

FIG. 9 is a side elevational view illustrating one of the plurality of resilient strips or wires for releasably retaining the sutures in folded condition on the implement of FIG. 1; and FIG. 10 is a side elevational view, and FIG. 10a is a sectional along lines a—a thereof, illustrating the two cover plates for securing the resilient strips of FIG. 9 to the implement of FIG. 1.

DESCRIPTION OF PREFERRED EMBODIMENTS

As indicated earlier, the implement illustrated in FIG. 1 is particularly useful in surgical operations for attaching a prosthetic valve by means of a plurality of "mattress" stitches each including a pledget for distributing over a large area the pressure applied by each stitch to the body annulus. This implement comprises: a manually-grippable handle 2 carrying a holder, generally designated 4, for releasably holding the member to be sutured, in this case a prosthetic valve PV (FIG. 2); pledget gripping means, generally designated 6, for gripping a plurality of pledgets P each in a position to be pierced by a suture needle; and suture retaining means, generally designated 8, for releasably retaining a plurality of sutures S in a folded condition on the handle. The illustrated implement is adapted to carry 16 sutures S and 16 pledgets P, with a suture needle SN attached to the opposite end of each suture.

FIG. 2 diagramatically illustrates the folded condition of each suture S. It will be seen that the suture needles SN at the opposite ends of each suture are located adjacent to the handle 2 of the implement, and remotely from the valve holder 4 end; each suture is formed with a plurality (in this case 6) folds, with each fold extending axially of the implement. One of the main advantages in the construction illustrated in FIG. 1 is that the implement may be pre-loaded with the prosthetic valve PV, the sutures S and the pledgets P. In this case one suture needle SN of each suture would pierce the valve PV and one side of pledget P, and the respective side of the suture would be formed with three folds before the suture needle is retained adjacent to the handle 2; and the opposite end of the respective suture S would similarly pierce the opposite side of its pledget P, there with three folds, and finally releasably retained adjacent to the handle 2.

Handle 2 is formed with a knob 10 at the end opposite to the valve holder 4. This knob may be rotated in one direction to cause holder 4 to grip the prosthetic valve PV and to cause the pledget gripping means 6 to grip the individual pledgets P; or the knob may be rotated in the opposite direction to cause holder 4 to release the valve, and to cause gripping means 6 to release the pledgets.

More particularly, the implement illustrated in FIG. 1 comprises a main body member 12, e.g. of plastic, having a configuration best seen in FIGS. 3 and 3a. Thus, it is formed with a bore 14 extending axially for its complete length, this bore being enlarged as shown as 14a, for the length of the body member between the one end thereof serving as the manually-grippable handle 2, and the opposite end to which the valve holder 4 is mounted. Between handle 2 and valve holder 4, body member 12 is formed with two annular ribs 16, 18, and a plurality of grooves 20 extending axially through annular ribs 16, 18 and the portion of body member 12 between these ribs.

Ribs 20 are each adapted to receive one of the resilient strips or wires 22 illustrated in FIG. 9 for retaining one of the sutures S in the folded condition as illustrated in FIG. 2. For this purpose, each groove 20 includes a main section 20a extending axially of the body member, and end sections 20b, 20c of greater depth and extending through the annular ribs 16, 18 of the body member. The intermediate section 20a of each rib 20 is dished and of decreasing depth towards its end portions 20b, 20c so as to define ledges 20d, 20e at the junctures of the intermediate section 20a with end sections 20b, 20c.

In the described embodiment, there are 32 such grooves 20, equally spaced around the circumference of the body member 12.

The structure of each of the resilient strips or wires 22 received in each of the grooves 20 is best seen in FIG. 9. Thus, each such resilient strip includes a main section 22a received within section 20a of its respective groove 20, and two end sections 22b, 22c received within the deeper end sections 20b, 20c, at the ends of its respective groove. The two end sections 22b, 22c terminate in a pair of radially-extending arms 22d, 22e each formed with a hooked tip 22f, 22g, engageable by the respective suture for retaining it in its folded condition as illustrated in FIG. 2. All the resilient wires 22 are secured to body 12 of the implement by a pair of curved cover plates 24a, 24b fixed by fasteners 24c (FIGS. 10 10a) and engaging the resilient strips at the ledges 20d, 20e of their respective grooves 20, with the end sections 22b, 22c of each strip received within the deep groove sections 20b, 20c.

The portion of body member 12 between its valve holder 4 end and its annular rib 16 is formed with three radially-extending bores 26. These bores receive pins 28 (FIG. 6) which are part of the pledget gripping means 6. Bores 26 are elongated in the axial direction to permit pins 28 to be moved in that direction in order to actuate the pledget gripping means 6, as will be described more particularly below.

The pledget gripping means 6 comprises a pair of annular members or rings 30, 32 received on the end 12a of body member 12 outwardly of its elongated bores 26. Annular member 30 is more particularly illustrated in FIGS. 4 and 4a; and annular member 32 is more particularly illustrated in FIGS. 5 and 5a. Member 30 is fixed to body member 12, as by fasteners 33 (or by a friction fit or threaded attachment); and member 32 is slidable over body member 12, towards and away from member 30, by the previously-mentioned pins 28 received within bores 26 of the body member.

As shown particularly in FIGS. 4 and 4a, annular member 30 is formed with a tapered end face 30a facing member 32, and with an annular array of slots 30b starting from tapered face 30a and terminating short of its opposite, flat face 30c. There are 32 such slots 30b, one for and aligned with each of the axial grooves 20 formed in the body member 12 for receiving the resilient strips 22. Member 32, particularly seen in FIGS. 5 and 5a, is also formed with a tapered end face 32a effective, when moved towards end face 30a of member 30, to grip the pledgets P between the two end faces. Member 32 is further formed with a circular array of axially-extending, circumferentially-spaced slots 32b alignable with slots 30b of member 30. Member 32 further includes a collar 32c receivable over body portion 14a and formed with radial bores 32d for receiving the previously-mentioned pins 28 passing through bores 26 of the body member. However, whereas bores 26 in body member 12a are axially-elongated, bores 30d in collar 32c member 32 are of the same diameter as the pins.

The face of member 32 opposite to its face 32a is formed with a plurality of bores for receiving pins 34 which are used for locating the pledgets P between the two annular member 30, 32. The illustrated design is intended to be used for 16 sutures, each suture being accommodated in two of the slots 30b, 32b of members 30 and 32, and therefore there would be 16 pins 36, one for every other slot, to accommodate 16 pledgets P, one for each of the sutures S.

It will be seen that when the two annular members 30, 32 are moved into firm engagement with each other, the pledgets P are securely gripped between them. Slots 30d in member 30, and slots 32b in member 32, serve as guides for guiding the sutures needles to pierce their respective pledgets. Thus, the suture needle SN at one end of a suture is guided by one pair of aligned slots 30b, 32b to pierce its respective pledgets at two points along one side of the pledget, and the needle SN at the opposite end of the respective suture is guided by the adjacent pair of slots 30b, 32b to pierce the pledget at two further points at the opposite side of the pledget.

The gripping end releasing of these pledgets P by moving annular member 32 towards and away from annular member 30 is effected by knob 10 at the opposite end of handle 2. For this purpose, knob 10 is secured to a central rod 40 which passes axially through the complete length of body member 12. The end of rod 40 adjacent to the valve holder 4 is of enlarged diameter, as shown at 40a, and its tip 40b is of reduced diameter for actuating holder 4 as will be described more particularly below.

The large-diameter end 40a of rod 40 is formed with external threads 40c threadedly received within a bore formed in holder 4.

Rod 40, adjacent to its enlarged-diameter end 40a, receives a short sleeve or ring 42 freely movable on the rod. As shown particularly in FIG. 7, ring 42 is formed with three radially-extending threaded bores 42a, one for each of the pins 28 (FIG. 6) which pins are formed with externally-threaded ends 28a received within bores 42a. The opposite (outer) end of each pin 28 is formed with a screw driver slot 28b.

Rod 40 further includes another ring 44 fixed to the rod, and a coil spring 46 interposed between fixed ring 44 and slidable ring 42. As will be described more particularly below, rotating knob 10 in one direction is effective to cause pin 28 to move member 32 into firm engagement with member 30, thus gripping the pledgets P between the two members; and rotating the knob in the opposite direction is effective to cause member 32 to release the pledgets from between the two members.

Valve holder 4 is secured to the end of body member 14 by means of an adaptor collar 50. The latter collar is press-fitted at one end into bore 14a of body member section 12a, and receives, by a press fit, valve holder 4.

Valve holder 4 includes a pair of jaws 51, 52 joined together by an end wall 54 formed with a threaded opening for receiving the threaded section 40a of rod 40. In addition, the two jaws 51, 52 are formed with shoulders 56, 58 facing each other but normally spaced apart a distance less than the diameter of tip 40d of rod 40. The outer faces of the two jaws 51, 52 are formed with an annular groove adapted to receive a rubber ring 59 for engagement with the inner face of prosthetic valve PV, which is of annular shape.

The implement illustrated in FIG. 1 further includes a retainer ring 60 between handle 2 and annular rib 18 for releasably retaining the suture needles SN. Retainer ring 60, more particularly illustrated in FIGS. 8 and 8a, is formed with a plurality of axially-extending slots 62, one for and aligned with each of the resilient strips 22 received in grooves 20 of the implement. Each slot 60 is formed with a narrow section 62a facing annular rib 18, and a wider section 62b facing handle 2. Ring 60 is secured to body portion 12 of the implement by a plurality of threaded pins 64. It will thus be seen that after one end of a suture S has been wound over arms 22d, 22e of the respective resilient member 22, its needle SN may be inserted within the wider section 62b of its respective slot 62, whereupon the end of the suture will be retained in place since the suture needle is of greater thickness than that of section 62a of the respective slot. Arms 22d, 22e are made resilient so as to accomodate variations in the length of the suture and also to maintain the suture under tension when its needle is received within its slot 62.

Ring 60 is further formed with a plurality of radially-extending bores, one between each pair of slots 62. A pin 66 is received within each of these bores 66. Thus, there would be one pin 66 for each slot 60; that is, one pin for each sewing needle SN. In the described example, there are 16 sutures each having a sewing needle at opposite ends, or a total of 32 sewing needles; and therefore there would be 32 slots 60 and 32 pin 66. These pins 66 are colour-coded according to their locations in the annular array formed by them. Thus, the annular array can be divided into four quadrants, each quadrant having a distinctive color. By thus color-coding the pins, the surgeon is better able to apply the sutures equally spaced around the body annulus, thereby decreasing the possibility of ending the suturing operation with wider-spaced or shorter-spaced sutures, which could increase the danger of valve leakage.

The suturing implement illustrated in the drawings is preferably used in the following manner.

Before the surgical operation, the implement is first pre-loaded with the prosthetic valve PV, the sutures S, and the pledgets P. For this purpose knob 10 is rotated in one direction such as to move the threaded section 40a of rod 40 leftwardly with respect to valve holder 4.

This causes the two jaws 51, 52 of the valve holder to move towards each other, by the inherent resiliency of their connecting end wall 54, thereby permitting a prosthetic valve to be applied around the two jaws. This movement of knob 10 also moves ring 42 in the direction such as to relieve sliding ring 44 from the pressure of the spring 46, whereupon pins 28 are moved away from annular member 32, thereby permitting the pledgets to be inserted between the pins 36. When the pledgets P and prosthetic valve PV have both been applied to the implement as described above, knob 10 is then rotated in the opposite direction, thereby causing the tip 40b of rod 40 to spread apart jaws 50, 52 to firmly grip the prosthetic valve PV. Ring 42 moves annular member 32, via spring 46, ring 44 and pins 28, to cause the pledgets P to be firmly gripped between members 30 and 32.

After the prosthetic valve and pledgets have thus been loaded, the implement is now loaded with the sutures S. For this purpose, the needle SN at one end of each suture is passed through the rim of the prosthetic valve PV around arm 22e of its respective resilient member 22 and back around arm 22d; then its needle is passed through groove 62a of ring 60 and is received within groove 62b of that ring. It will thus be seen that this end of the suture forms three folds between its pledget P and ring 60. The opposite end of the same suture S is similarly wound around arms 22e and 22d of the next adjacent resilient strip 22, and is then received within the next adjacent slots 62a, 62b of ring 60. The remaining sutures are similarly loaded, each one passing through the rim of the prosthetic valve PV within holder 4, and secured between annular members 30, 32.

The above-described procedure is performed before the surgical operation, for example by the manufacturer supplying the implement preloaded with the prosthetic valve PV, plegets P and sutures S.

During the surgical operation, the natural, defective valve is surgically removed from the patient, and the annulus is prepared for receiving the prosthetic valve PV. Implement 2, pre-loaded with the prosthetic valve, pledgets and sutures, is held by an attendant over the subject's body with the prosthetic valve facing, but spaced a distance from, the annulus of the patient. Each suture is then applied to the body annulus by first removing its needle SN at one end of the suture from ring 60, unfolding the suture from arms 22d, 22e, passing the needle through the body annulus. The needle is then passed through its respective pledget P, the needle being guided by slots 30b, 32b in annular members 30, 32 as it pierces two points along one side of its respective pledget. The needle is then returned to its slot in ring 60. The needle SN at the opposite end of the respective suture is similarly removed from ring 60, applied through the body annulus, through the opposite side of its respective pledget, and then returned to the ring.

After the first suture has thus been applied, an attendant holding handle 2 of the implement lightly pulls it away from the body annulus to thereby apply a traction force retracting the annulus and also placing the so-applied suture under tension.

All the remaining sutures are then applied in the same manner as described above, one after the other, while the attendant maintains the traction force on the implement to retract the annulus and to tension each suture after it has been applied in its turn.

After all the sutures have been so applied (sixteen sutures in the example described above), and while all the sutures are maintained under tension by the traction force applied to handle 2 by the attendant, knob 10 is rotated in order to withdraw tip 40b of rod 40 from between the jaw shoulders 56, 58, thereby permitting the jaws 51, 52 to move together, under the inherent resiliency of their connecting end-wall 54, to release the prosthetic valve PV gripped by these jaw. This rotation of knob 10 also moves pins 28 (leftwardly in FIG. 1), releasing member 32 from gripping the pledgets P between this member and member 30. The surgeon may then remove all the pledgets from between members 30, 32, grasp the prosthetic valve PV between his thumb and index finger, and slide the valve along the tensioned sutures S towards the patient and into the body annulus, with all the plegets P disposed on the outer side of the body annulus. Each suture is then tied in place by first releasing its opposite ends from ring 60 and forming one or more knots along the outer side of the body annulus, to securely hold the valve within the annulus. After all the sutures have thus been secured, the free ends of the sutures are trimmed.

It will thus be seen that using the implement illustrated in the drawings for surgically attaching a prosthetic valve as described above provides a number of important advantages over the existing techniques, including the following: since the implement is preloaded before the operation with the valve, sutures and pledgets, substantially less time is required during the actual surgical operation for attaching the valve to the body annulus; the implement serves as a common retractor for exposing the complete annulus during the operation; the tensioned sutures act as a guide for guiding the valve into proper position within the heart annulus, thereby better assuring correct placement of the valve in a minimum of time; and there is substantially less danger of entanglement of the sutures, since they are maintained in folded condition before their use, and when unfolded they are always maintained under tension. Still further advantages are: this implement permits the knots to be made along the outer edge of the body annulus to overlie the pledgets, thereby decreasing the danger of interfering with the valve and causing valve mal-function or leakage; and the uniform placement of the sutures around the body annulus is better assured by the provision of the color-coded pins 64 in the needle retainer ring 60, thereby further decreasing the danger of valve leakage.

While the invention has been described particularly for use in surgical operations for the attachment of prosthetic valves, it will be appreciated that the invention could also be used in other applications. For example, it could be used for attaching a patch over a ventricular or septal defect, wherein the holder (4) would be one designed to hold the patch and the tensioned sutures would guide the patch to proper position over the defect. The invention could also be used in other sewing, but non-surgical, applications, wherein the capability of the implement for precisely placing the member to be sewn is advantageously utilized.

Many other variations, modifications and applications of the invention may be made.

What is claimed is:

1. A suturing implement particularly useful in surgical operations for suturing a member, such as a prosthetic valve, to tissue at the suture site by a plurality of sutures each including a needle attached to at least one end thereof, comprising:

a manually grippable handle;

pledget gripping means carried by said handle for gripping a plurality of pledgets each in a position to be pierced by a suture needle;

and releasing means carried by said handle for actuating said pledget gripping means to release said pledgets and the sutures applied thereto from said handle.

2. The suturing implement according to claim 1, wherein said pledget gripping means grips said plurality of pledgets while in the form of an annular array around said handle.

3. The suturing implement according to claim 2, wherein said pledget gripping means comprises a pair of annular members adapted to receive between them said annular array of pledgets, one of said annular members being movable by said releasing means toward and away from the other annular member to grip and to release, respectively, said plurality of pledgets.

4. The implement according to claim 3, wherein said pair of annular members comprise axially-extending grooves for guiding the suture needle when applied to pierce the pledgets.

5. The implement according to claim 1, further including suture retaining means for releasably retaining a plurality of sutures in folded condition on said handle.

6. The implement according to claim 5, wherein said suture retaining means retains said plurality of sutures in the form of an annular array on said handle with the sutures spaced circumferentially from each other and folded axially with respect to said handle.

7. The implement according to claim 6, wherein said suture retaining means comprises a plurality of circumferentially-spaced strips each extending axially of the handle and formed with a pair of radially-extending resilient arms at its opposite ends for retaining the sutures in said folded condition.

8. The implement according to claim 7, wherein said strips are of resilient material and include intermediate portions integrally formed with said arms and received in axially-extending grooves in said handle.

9. The implement according to claim 8, wherein said suture retaining strips are secured by outer cover plates fixed to said handle to overly said intermediate portions of said strips.

10. The implement according to claim 6, wherein said suture retaining means further comprises an annular ring secured to said handle and formed with an annular array of slots for receiving the suture needles at the ends of the sutures.

11. The implement according to claim 1, further including a holder at one end of the handle for releasably holding the member to be sutured.

12. The implement according to claim 11, wherein said member to be sutured is an annular prosthetic valve, and said holder comprises a pair of jaws receivable within said prosthetic valve and movable apart to grip same, or towards each other to release same.

13. The implement according to claim 12, wherein said jaws are movable toward and away from each other by a pin, and said holder further includes:

an end wall secured to one end of said pair of jaws;

a mounting collar secured to said end wall and formed with an aperture for receiving said pin therethrough;

and a pair of shoulders formed at an intermediate location on said jaws;

said shoulders being aligned with each other but spaced apart a distance less than the thickness of said pin such that moving said pin axially of said jaws into engagement with said shoulders causes the jaws to move away from each other to grip said prosthetic valve, whereas moving said pin in the opposite direction away from said shoulders causes the jaws to move towards each other, to release said prosthetic valve, by the resiliency of said end wall.

14. An implement according to claim 13, wherein said holder comprises an adapter collar carrying said jaws and attachable to said handle to facilitate applying different holders for different size prosthetic valves to said handle.

15. The implement according to claim 13, wherein said pin for moving said jaws is actuated by said releasing means carried by said handle for actuating the pledget gripping means.

16. The implement according to claim 13, wherein said releasing means comprises a knob at one end of said handle rotatable in one direction to cause the pledget gripping means to grip the pledgets and the holder to grip the prosthetic valve, said knob being rotatable in the opposite direction to cause the pledget gripping means to release the pledgets, and the holder to release the prosthetic valve.

17. The implement according to claim 13, wherein said suture retaining means includes indicia dividing the annular array of sutures into a plurality of sections each separately identified to assist the surgeon in applying the sutures around the body annulus with equal spacings.

18. The implement according to claim 17, wherein said indicia comprise a plurality of colour-coded pins disposed around the handle.

19. The implement according to claim 13, wherein said handle is pre-loaded with said pledgets, sutures and prosthetic valve.

* * * * *